(12) United States Patent
Brock et al.

(10) Patent No.: US 6,398,822 B1
(45) Date of Patent: Jun. 4, 2002

(54) PACKAGED HAIR COLORING COMPOSITION

(75) Inventors: Earl David Brock, West Chester; Heather Holden Harper, Hamilton, both of OH (US); Taher Iqbal Yousaf, Egham Surrey (GB)

(73) Assignee: The Proctor & Gamble Company, Cincinnati, OH (US)

( * ) Notice: Subject to any disclaimer, the term of this patent is extended or adjusted under 35 U.S.C. 154(b) by 0 days.

(21) Appl. No.: 09/647,577

(22) PCT Filed: Apr. 1, 1999

(86) PCT No.: PCT/US99/07285
§ 371 (c)(1),
(2), (4) Date: Dec. 18, 2000

(87) PCT Pub. No.: WO99/51195
PCT Pub. Date: Oct. 14, 1999

Related U.S. Application Data

(63) Continuation of application No. PCT/US98/06582, filed on Apr. 2, 1998.

(51) Int. Cl.$^7$ .................................................. A61K 7/13
(52) U.S. Cl. ................. 8/428; 8/543; 8/549; 8/642; 8/685; 8/918; 540/126; 544/180; 544/224; 544/242; 534/634; 534/637; 534/638
(58) Field of Search ............................ 8/428, 543, 549, 8/685, 918, 642; 540/126; 544/180, 224, 242; 534/634, 637, 638

(56) References Cited

U.S. PATENT DOCUMENTS

| | | | |
|---|---|---|---|
| 5,548,071 A | | 8/1996 | Deitz et al. ................. 534/612 |
| 5,735,911 A | * | 4/1998 | Tzikas ............................ 8/547 |
| 5,760,193 A | * | 6/1998 | Russ et al. ................... 534/605 |
| 5,780,602 A | * | 7/1998 | Schumacher et al. ....... 534/642 |
| 5,785,745 A | * | 7/1998 | Lauw et al. ............. 106/31.27 |
| 5,914,444 A | * | 6/1999 | Reinert et al. .................. 8/442 |
| 5,944,855 A | * | 8/1999 | Lehmann et al. .............. 8/549 |
| 5,958,086 A | * | 9/1999 | Adam et al. .................... 8/641 |
| 5,968,208 A | * | 10/1999 | Taylor ............................ 8/543 |
| 5,976,197 A | * | 11/1999 | Hutchings et al. ............. 8/543 |
| 6,159,250 A | * | 12/2000 | Patsch ........................... 8/549 |

FOREIGN PATENT DOCUMENTS

DE 19962228 * 12/1999

* cited by examiner

Primary Examiner—Lorna M. Douyon
Assistant Examiner—Ann-Marie Koss
(74) Attorney, Agent, or Firm—Brent M. Peebles; Brahm J. Corstanje; Tara M. Rosnell

(57) ABSTRACT

Packaged hair coloring composition comprising a stable aqueous hair coloring composition comprising a compound of formula (I):

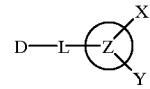

wherein the variables are each as defined in the claims. The packaged hair coloring compositions of the present invention provide improved wash fastness of dye on hair, less color fade over time, improved consumer acceptance in terms of providing a single packaged hair dye composition and improved product stability.

11 Claims, No Drawings

PACKAGED HAIR COLORING COMPOSITION

This application is a 371 of PCT/US99/07285 filed Apr. 1, 1999 and a con. of PCT/US98/06582 filed Apr. 2, 1998.

TECHNICAL FIELD

This invention relates to a packaged hair colouring composition comprising a reactive dye compound comprising a chromophore and a nitrogen-containing heterocycle comprising at least one thio-substituent.

BACKGROUND OF THE INVENTION

The desire to alter the color of human hair is not a facet of modern times. Since the days of the Roman Empire the color of human hair has been routinely altered to accommodate the changes of fashion and style. However the attainment of precise initial colors which are retained by the hair for a desirable period has remained a more elusive goal. The difficulties in the development of hair coloring compositions which can deliver precise long-lasting colors are in part due to the inherent structure of the hair itself and in part due to the necessary conditions of effective hair coloration processes.

In general, the condition and structure of human hair is not regular along the length of the hair shaft. Human hair is subject to various chemical and mechanical treatments such as combing, brushing, shampooing, heating, perming as well as exposure to the sun. As such, the hair at the ends of the hair shaft will generally exhibit greater signs of damage relative to the new growth close to the scalp. This damage can lead to inconsistent coloration when the hair is dyed due to irregular uptake of the hair coloring agents along the length of the hair shaft.

Once the hair has been colored there is a desire for the color to be resistant to fading, as occasioned by the actions of washing (also known as wash fastness), perspiration, hair spray and other exterior factors such as the action of the sun, and further that the color be retained in a consistent manner for a predictable period of time. Additionally damage to the hair that can lead to irregular dye uptake as discussed above, can lead to increased fading of the damaged portions of the hair and consequently, irregular levels of color fade over time. An additional difficulty commonly associated with the dyeing of human hair is the need for dye systems which avoid any adverse effect on the hair and skin of the user, such as brittle hair, or, irritation of the skin, or, staining (coloring) of the skin.

Thus, it would be desirable to develop a hair coloring composition which exhibits reduced fade, provides improved resistance to wash out during a regular cleansing regimen, can deliver substantially consistent hair color results throughout the hair, which has reduced irritant effect on the skin, which has reduced staining on the skin, which has reduced adverse effects on the hair of the user and also to develop a convenient and easy-to-use method for the delivery of such a hair coloring composition to the hair.

Over the years significant effort has been directed towards the elimination of many of the problems associated with the dyeing of human hair. Various approaches to hair dyeing have been developed, these include, oxidative dyes, direct action dyes, natural dyes, metallic dyes and reactive dyes.

GB-A-0,951,021 (Turner-Hall Corporation) relates to methods and compositions for dyeing keratinous fibres by attaching a dyestuff molecule to a particular site thereof through true covalent bonds. The method comprises reducing some of the disulfide linkages of the cystine in the fibers to sulfhydryl groups while breaking hydrogen bonds by applying to the fibers in alkaline aqueous solution a reducing agent for breaking disulfide linkages of keratinous fibres and a hydrogen bond breaker for keratinous fibres and bonding a water-soluble fibre reactive dye compound such as a dichlorotriazine dye to the sulfhydryl groups by applying an aqueous solution of the fibre reactive dye. Thioglycolic acid is disclosed as a reducing agent.

U.S. Pat. No. 3,415,606 discloses a method for dyeing human hair comprising the steps of treating said hair with an effective amount of mercaptan and then treating the hair with a dichlorotriazine fibre reactive dye.

"The Reaction Mechanism of Fibre Reactive Dyestuffs with Hair Keratin", Albert Shansky, American Perfumer and Cosmetics, November 1966, and "Dyeing of Human Hair with Fibre Reactive Dyestuffs", Albert Shansky, Cosmetics and Toiletries, November 1976, disclose a method of coloring hair comprising treating the hair for five minutes with a reducing-H bond breaking solution (containing thioglycolate, alkali, lithium bromide and urea) followed by rinsing the hair and then treating the hair with a dichlorotriazine fibre reactive dye.

Dyes and Pigments 14, 1990, pages 239–263, "Synthesis and Application of Reactive Dyes with Heterocyclic Reactive Systems" discloses fibre reactive dyes containing chlorotriazine heterocycles with thio substituents.

Reactive dye hair coloring agents can be used to deliver a variety of hair colors to the hair. However substantial improvement is needed in the areas of color saturation, color development, precise initial color consistency, improved wash fastness, improved hair condition and levels of hair damage.

Thus there is a need for reactive dye hair coloring compounds and compositions which effectively dye the hair but avoid or reduce damage to the hair, which can color the hair effectively and avoid or reduce irritation and/or staining to the skin of the user.

It has surprisingly been found that the packaged hair colouring compositions of the present invention comprising a nitrogen-containing heterocycle selected from pyrimidine or triazine, substituted with at least one thio-derivative, provides improvements in colour saturation, colour development, colour consistence, wash fastness, hair condition, and reduction in hair damage and skin irritation.

In addition, conventional, reactive dye hair coloring compositions typically comprise at least two separately packaged components, which are generally, reducing agent and reactive dye hair coloring agents. These separately packaged components are admixed just prior to application to the hair. Such an admixing step can be messy and inconvenient to the user. Typically, such coloring compositions need to be used soon after admixing due to degradation of the resulting coloring composition. As such, excess admixed coloring composition is disposed of after application of the required amount to the hair. It has been found that the reactive dyes of the present invention can be incorporated in a singly packaged mixture with improved stability versus conventional reactive dye systems. The singly packaged coloring compositions of the present invention are suitable for use in a multi-application format (i.e. the consumer can use a single package for several color applications over a period of time). It has also been found that the reactive dye compounds and compositions herein are stable over time, and can be stored as such.

All percentages are by weight of the final compositions in the form intended to be used unless specified otherwise.

SUMMARY OF THE INVENTION

According to the present invention there is provided packaged hair colouring composition comprising a stable aqueous hair colouring composition comprising a compound of formula (I):

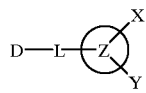

wherein D is a chromophore;

X and Y are independently selected from halogen and —SR', provided that at least one of X and Y is —SR', wherein R' is selected from H, $C_1$–$C_4$ alkyl, $(CH_2)_n$COOH, $(CH_2)_n$CONH$_2$, $(CH_2)_n$SO$_3$H, $(CH_2)_n$COOM, $(CH_2)_n$PO$_3$H, $(CH_2)_n$OH, $(CH_2)_n$SSO$_3^-$, $(CH_2)_n$NR''$_2$, $(CH_2)_n$N$^+$R''$_3$, PhSSO$_3^-$, PhSO$_3$H, PhPO$_3$H, PhNR''$_2$, PhN$^+$R''$_3$, —CN, SO$_3^-$, $(CH_2)_2$CH(SH)R''$(CH_2)_3$COOH, —CH$_2$CHOHCH$_2$SH, and

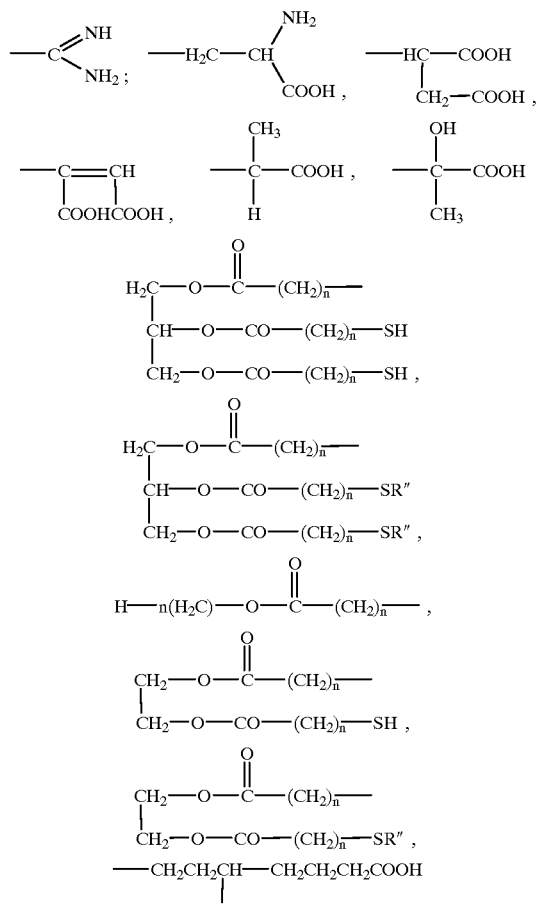

—CH$_2$CH$_2$NH$_2$ n is an integer in the range of 1 to 4 wherein within the same molecule n is not necessarily the same integer; and M is a cation of alkaline earth metal, alkali metal, NH$_4^+$ or NR''$_3^+$;

L is a linking moiety;

Z is selected from pyrimidine or triazine;

R'' is C1–C4 alkyl;

and a package for said hair colouring composition.

The packaged hair colouring compositions of the present invention provide improved wash fastness of dye on hair, less colour fade over time, improved consumer acceptance in terms of providing a single packaged hair dye composition and improved product stability.

DETAILED DESCRIPTION OF THE INVENTION

The packaged hair colouring composition of the present invention comprises a hair colouring composition comprising a reactive dye compound and a package for said hair colouring composition.

Any suitable packaging for delivering the reactive dye compounds and compositions described herein can be used. Examples of suitable packaging include bottle, pump-foamer, and the like.

The hair colouring composition comprises a reactive dye which comprises a nitrogen-containing heterocycle, a chromophore moiety, a linking group to link the nitrogen-containing heterocycle to the chromophore.

The reactive dye compounds used herein have the formula (I):

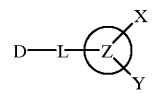

wherein D is a chromophore;

X and Y are independently selected from halogen and —SR', provided that at least one of X and Y is —SR', wherein R' is selected from H, $C_1$–$C_4$ alkyl, $(CH_2)_n$COOH, $(CH_2)_n$CONH$_2$, $(CH_2)_n$SO$_3$H, $(CH_2)_n$COOM, $(CH_2)_n$PO$_3$H, $(CH_2)_n$OH, $(CH_2)_n$SSO$_3^-$, $(CH_2)_n$NR''$_2$, $(CH_2)_n$N$^+$R''$_3$, PhSSO$_3^-$, PhSO$_3$H, PhPO$_3$H, PhNR''$_2$, PhN$^+$R''$_3$, —CN, SO$_3^-$, $(CH_2)_2$CH(SH)R''$(CH_2)_3$COOH, —CH$_2$CHOHCH$_2$SH, and

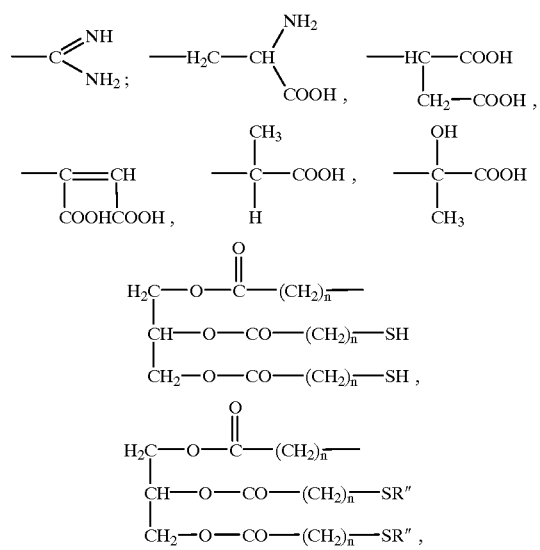

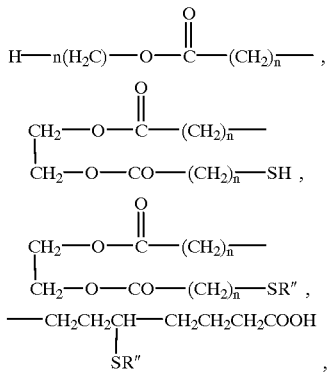

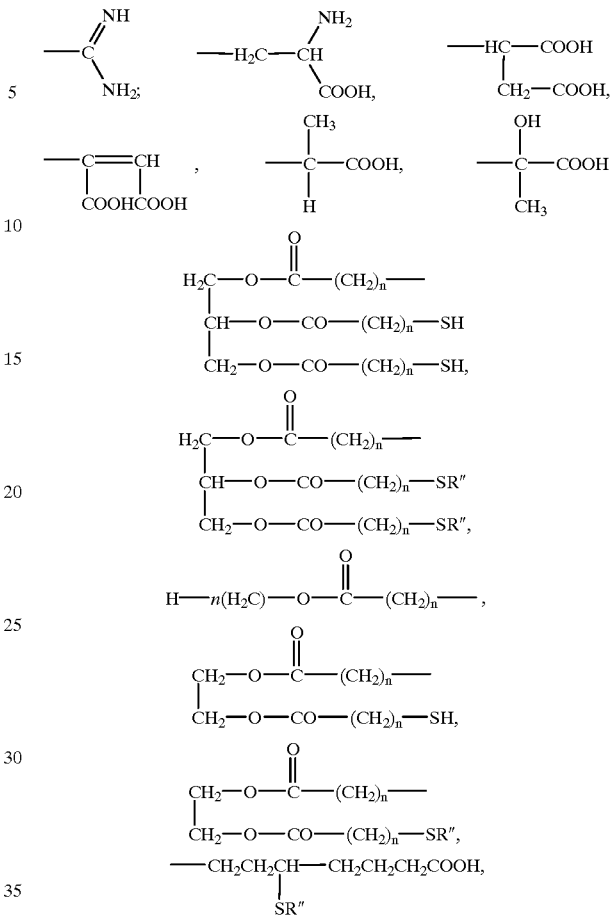

—CH₂CH₂NH₂ n is an integer in the range of 1 to 4 wherein within the same molecule n is not necessarily the same integer; and M is a cation of alkaline earth metal, alkali metal, $NH_4^+$ or $NR''_3^+$;

L is a linking moiety;

Z is selected from pyrmidine or triazine;

R" is C1–C4 alkyl;

and esters and salts thereof.

Chromophore Moiety

Any chromophore moieties suitable for use for dying substrates can be used in the present invention. The term chromophore as used herein means any photoactive compound and includes any coloured or non-coloured light absorbing species, e.g. fluorescent brighteners, UV absorbers, IR absorbing dyes.

Suitable chromophore moieties for use in the dye compounds herein include the radicals of monoazo, disazo or polyazo dyes or of heavy metal complex azo dye derived therefrom or of an anthraquinone, phthalocyanine, formazan, azomethine, dioxazine, phenazine, stilbene, triphenylmethane, xanthene, thioxanthene, nitroaryl, naphthoquinone, pyrenequinone or perylenetetracarbimide dye.

Suitable chromophore moieties for use in the dye compounds herein include those disclosed in EP-A-0,735,107 (Ciba-Geigy), incorporated herein by reference, including the radicals described therein which contain substituents customary for organic dyes, such as sulphonate substituents which enhance the water-soluble properties of the dye compound.

Most preferred chromophore D groups for use herein are polysulphonated azo chromophores such as those present in Levafix (RTM) dyes commercially available from Dystar.

Nitrogen Containing Heterocycle

The nitrogen containing heterocycle herein is selected from pyrimidine or triazine, preferably triazine.

The nitrogen containing heterocycle has at least one thio substituent SR' wherein R' is selected from H, $C_1$–$C_4$ alkyl, $(CH_2)_n COOH$, $(CH_2)_n CONH_2$, $(CH_2)_n SO_3 H$, $(CH_2)_n COOM$, $(CH_2)_n PO_3 H$, $(CH_2)_n OH$, $(CH_2)_n SSO_3^-$, $(CH_2)_n NR''_2$, $(CH_2)_n N^+R''_3$, $PhSSO_3^-$, $PhSO_3 H$, $PhPO_3 H$, $PhNR''_2$, $PhN^+R''_3$, —CN, $SO_3^-$, $(CH_2)_2 CH(SH)R''(CH_2)_3 COOH$, —$CH_2CHOHCH_2SH$, and

—CH₂CH₂NH₂ n is an integer in the range of 1 to 4 wherein within the same molecule n is not necessarily the same integer; and M is a cation of alkaline earth metal, alkali metal, $NH_4^+$ or $NR''_3^+$.

Preferred R' groups for use herein are CH2COOH, CH2CH2OH and (COOH) CH2CH2(COOH), preferably CH2COOH.

The nitrogen-containing heterocycle may be substituted by two SR' groups or by one SR' group and one halogen group, preferably by two SR' groups.

Linking Moiety

The compounds herein further comprise a linking moiety to link each nitrogen-containing heterocycle to each chromophore moiety. Any linking moieties suitable for use in dyeing substrates can be used in the present invention. Preferably the linking moiety is selected from NR, NRC=O, C(O)NR, NRSO₂ and —SO₂NR wherein R is H or $C_1$–$C_4$ alkyl which can be substituted by halogen, preferably fluorine or chlorine, hydroxyl, cyano, $C_1$–$C_4$ alkoxy, $C_2$–$C_5$ alkoxycarbonyl, carboxyl, sulfamoyl, sulfo or sulfato. When the heterocycle is quinoxaline or phthalazine, a preferred linking moiety is NRC=O, where R is H or C1–C4 alkyl, more preferably where R is H or CH₃, especially H.

In general, dyes having the formula (I) can be prepared by reacting suitable precursors of the dye of formula (I) with one another, at least one of which contains a group D-L-Z, wherein D, L and Z are as defined above, at least one of which contains an SR' group (wherein R' is as defined above).

For example, dye compounds of the invention having a formula (I) wherein Z is a triazine heterocycle can be prepared by reacting one mole of dichlorotriazine dye, such as those commercially available from BASF under the tradename Procion (RTM), with a one mole of a suitable reactant containing an SR' group.

Dye compounds of the invention having a formula (I) wherein Z is a pyrimidine heterocycle can be prepared by reacting a difluoromonochloro pyrimidine dye such as those commercially available from Clariant under the tradenames Drimalan F (RTM) and Drimarene R or K (RTM), or a trichloropyrimidine dye such as those commercially available from Clariant under the tradename Drimarene X, with a suitable reactant containing an SR' group.

The reactions of the starting dye compounds with the reactant containing an SR' group are generally carried out at a pH of from about 7 to about 10, and at a temperature of about 0–5 C.

The dye compounds herein can be incorporated into dye compositions together with suitable carrier materials which are selected depending on what type of substrate is being dyed. Such carrier materials will be well known to those skilled in the art.

Any carrier materials suitable for use in hair dye compositions can be used herein.

The compositions of the present invention comprise from about 0.01% to about 10%, preferably from about 0.1% to about 5%, especially from about 0.1% to about 3% by weight of one or more reactive dye compounds having the formula (I). The types and levels of dyes used in each composition will depend upon the desired hair shade.

A preferred ingredient in the hair dye compositions herein is a reducing agent. Any reducing agents suitable for use in hair dye compositions may be used herein. Some typical reducing agents for use herein are listed in GB-A-951,021 and GB-A-589,956, incorporated herein by reference. Examples of suitable reducing agents include thioglycolic acid, thiolactic acid, dihydrolipoate, thioglycerol, mercaptopropionic acid, sodium bisulfite, ammonium bisulfide, zinc formaldehyde sulfoxylate, sodium formaldehyde sulfoxylate, sodium metabisulfite, potassium borohydride, pegylated thiols and hydroquinone. Particularly suitable for use herein are pegylated thiols.

Another preferred ingredient herein is a hydrogen bond breaker. Any hydrogen bond breaker suitable for use in a hair dye composition can be used herein. Suitable examples include lithium bromide, urea, resorcinol, catechol, dihydroxyacetone, formamide, potassium chloride and magnesium chloride. Particularly preferred for use herein is urea.

The coloring compositions of the present invention have a pH in the range of from about 7 to about 11, preferably from about 9 to about 10.5. In order to maintain such a pH the compositions may contain one or more optional buffering agents.

Examples of alkaline buffering agents are ammonium hydroxide, ethylamine, dipropylamine, triethylamine and alkanediamines such as 1,3-diaminopropane, anhydrous alkaline alkanolamines such as, mono or di- ethanolamine, preferably those which are completely substituted on the amine group such as dimethylaminoethanol, polyalkylene polyamines such as diethylenetriamine or a heterocyclic amine such as morpholine as well as the hydroxides of alkali metals, such as sodium and potassium hydroxide, hydroxides of alkali earth metals, such as magnesium and calcium hydroxide, basic amino acids such as L-argenine, lysine, alanine, leucine, iso-leucine, oxylysine and histidine and alkanolamines such as dimethylaminoethanol and aminoalkylpropanediol and mixtures thereof. Also suitable for use herein are compounds that form $HCO_3^-$ by dissociation in water (hereinafter referred to as 'ion forming compounds'). Examples of suitable ion forming compounds are $Na_2CO_3$, $NaHCO_3$, $K_2CO_3$, $(NH_4)_2CO_3$, $NH_4HCO_3$, $CaCO_3$ and $Ca(HCO_3)$ and mixtures thereof.

Preferred buffering agents for use herein are ammonium hydroxide, and sodium hydroxide.

The coloring compositions of the present invention may additionally include a thickener at a level of from about 0.05% to about 20%, preferably from about 0.1% to about 10%, more preferably from about 0.5% to about 5% by weight. Thickening agents suitable for use in the compositions herein are selected from oleic acid, cetyl alcohol, oleyl alcohol, sodium chloride, cetearyl alcohol, stearyl alcohol, synthetic thickeners such as Carbopol, Aculyn and Acrosyl and mixtures thereof. Preferred thickeners for use herein are Aculyn 22 (RTM), steareth-20 methacrylate copolymer; Aculyn 44 (RTM) polyurethane resin and Acusol 830 (RTM), acrylates copolymer which are available from Rohm and Haas, Philadelphia, Pa., USA. Additional thickening agents suitable for use herein include sodium alginate or gum arabic, or cellulose derivatives, such as methyl cellulose or the sodium salt of carboxymethylcellulose or acrylic polymers.

Water is the preferred diluent for the compositions according to the present invention. However, the compositions according to the present invention may include one or more solvents as additional diluent materials. Generally, solvents suitable for use in the coloring compositions of the present invention are selected to be miscible with water and innocuous to the skin. Solvents suitable for use as additional diluents herein include $C_1$–$C_{20}$ mono- or polyhydric alcohols and their ethers, glycerine, with monohydric and dihydric alcohols and their ethers preferred. In these compounds, alcoholic residues containing 2 to 10 carbon atoms are preferred. Thus, a preferred group includes ethanol, isopropanol, n-propanol, butanol, propylene glycol, ethylene glycol monoethyl ether, and mixtures thereof. Water is the preferred principal diluent in the compositions according to the present invention. Principal diluent, as defined herein, means, that the level of water present is higher than the total level of any other diluents.

The diluent is present at a level preferably of from about 5% to about 99.98%, preferably from about 15% to about 99.5%, more preferably at least from about 30% to about 99%, and especially from about 50% to about 98% by weight of the compositions herein.

The compositions of the present invention can additionally contain a surfactant system. Suitable surfactants for inclusion in the compositions of the invention generally have a lipophilic chain length of from about 8 to about 22 carbon atoms and can be selected from anionic, cationic, nonionic, amphoteric, zwitterionic surfactants and mixtures thereof.

(i) Anionic Surfactants

Anionic surfactants suitable for inclusion in the compositions of the invention include alkyl sulphates, ethoxylated alkyl sulphates, alkyl glyceryl ether sulfonates, methyl acyl taurates, fatty acyl glycinates, N-acyl glutamates, acyl isethionates, alkyl sulfosuccinates, alkyl ethoxysulphosuccinates, alpha-sulfonated fatty acids, their salts and/or their esters, alkyl ethoxy carboxylates, alkyl phosphate esters, ethoxylated alkyl phosphate esters, alkyl sulphates, acyl sarcosinates and fatty acid/protein condensates, and mixtures thereof. Alkyl and/or acyl chain lengths for these surfactants are $C_{12}$–$C_{22}$, preferably $C_{12}$–$C_{18}$ more preferably $C_{12}$–$C_{14}$.

(ii) Nonionic Surfactants

The compositions of the invention can also comprise water-soluble nonionic surfactant(s). Surfactants of this class include $C_{12}$–$C_{14}$ fatty acid mono- and diethanolamides, sucrose polyester surfactants and polyhydroxy fatty acid amide surfactants having the general formula below.

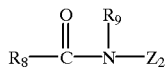

The preferred N-alkyl, N-alkoxy or N-aryloxy, polyhydroxy fatty acid amide surfactants according to the above formula are those in which $R_8$ is $C_5$–$C_{31}$ hydrocarbyl, preferably $C_6$–$C_{19}$ hydrocarbyl, including straight-chain and branched chain alkyl and alkenyl, or mixtures thereof and $R_9$ is typically hydrogen, $C_1$–$C_8$ alkyl or hydroxyalkyl, preferably methyl, or a group of formula —$R^1$—O—$R^2$ wherein $R^1$ is $C_2$–$C_8$ hydrocarbyl including straight-chain, branched-chain and cyclic (including aryl), and is preferably $C_2$–$C_4$ alkylene, $R^2$ is $C_1$–$C_8$ straight-chain, branched-chain and cyclic hydrocarbyl including aryl and oxyhydrocarbyl, and is preferably $C_1$–$C_4$ alkyl, especially methyl, or phenyl. $Z_2$ is a polyhydroxyhydrocarbyl moiety having a linear hydrocarbyl chain with at least 2 (in the case of glyceraldehyde) or at least 3 hydroxyls (in the case of other reducing sugars) directly connected to the chain, or an alkoxylated derivative (preferably ethoxylated or propoxylated) thereof. $Z_2$ preferably will be derived from a reducing sugar in a reductive amination reaction, most preferably $Z_2$ is a glycityl moiety. Suitable reducing sugars include glucose, fructose, maltose, lactose, galactose, mannose, and xylose, as well as glyceraldehyde. As raw materials, high dextrose corn syrup, high fructose corn syrup, and high maltose corn syrup can be utilised as well as the individual sugars listed above. These corn syrups may yield a mix of sugar components for $Z_2$. It should be understood that it is by no means intended to exclude other suitable raw materials. $Z_2$ preferably will be selected from the group consisting of —$CH_2$—$(CHOH)_n$—$CH_2OH$, —$CH(CH_2OH)$—$(CHOH)_{n-1}$—$CH_2H$, $CH_2(CHOH)_2(CHOR')CHOH)$—$CH_2OH$, where n is an integer from 1 to 5, inclusive, and R' is H or a cyclic mono- or polysaccharide, and alkoxylated derivatives thereof. As noted, most preferred are glycityls wherein n is 4, particularly —$CH_2$—$(CHOH)_4$—$CH_2OH$.

The most preferred polyhydroxy fatty acid amide has the formula $R_8(CO)N(CH_3)CH_2(CHOH)_4CH_2OH$ wherein $R_8$ is a C6–C19 straight chain alkyl or alkenyl group. In compounds of the above formula, $R_8$—CO—N< can be, for example, cocoamide, stearamide, oleamide, lauramide, myristamide, capricamide, palmiamide, tallowamide, etc.

Suitable oil derived nonionic surfactants for use herein include water soluble vegetable and animal-derived emollients such as triglycerides with a polyethyleneglycol chain inserted; ethoxylated mono and di-glycerides, polyethoxylated lanolins and ethoxylated butter derivatives. One preferred class of oil-derived nonionic surfactants for use herein have the general formula below:

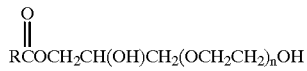

wherein n is from about 5 to about 200, preferably from about 20 to about 100, more preferably from about 30 to about 85, and wherein R comprises an aliphatic radical having on average from about 5 to 20 carbon atoms, preferably from about 7 to 18 carbon atoms.

Suitable ethoxylated oils and fats of this class include polyethyleneglycol derivatives of glyceryl cocoate, glyceryl caproate, glyceryl caprylate, glyceryl tallowate, glyceryl palmate, glyceryl stearate, glyceryl laurate, glyceryl oleate, glyceryl ricinoleate, and glyceryl fatty esters derived from triglycerides, such as palm oil, almond oil, and corn oil, preferably glyceryl tallowate and glyceryl cocoate.

Preferred for use herein are polyethyleneglycol based polyethoxylated $C_9$–$C_{15}$ fatty alcohol nonionic surfactants containing an average of from about 5 to about 50 ethyleneoxy moieties per mole of surfactant.

Suitable polyethylene glycol based polyethoxylated $C_9$–$C_{15}$ fatty alcohols suitable for use herein include $C_9$–$C_{11}$ Pareth-3, $C_9$–$C_{11}$ Pareth-4, $C_9$–$C_{11}$ Pareth-5, $C_9$–$C_{11}$ Pareth-6, $C_9$–$C_{11}$ Pareth-7, $C_9$–$C_{11}$ Pareth-8, $C_{11}$–$C_{15}$ Pareth-3, $C_{11}$–$C_{15}$ Pareth-4, $C_{11}$–$C_{15}$ Pareth-5, $C_{11}$–$C_{15}$ Pareth-6, $C_{11}$–$C_{15}$ Pareth-7, $C_{11}$–$C_{15}$ Pareth-8, $C_{11}$–$C_{15}$ Pareth-9, $C_{11}$–$C_{15}$ Pareth-10, $C_{11}$–$C_{15}$ Pareth-11, $C_{11}$–$C_{15}$ Pareth-12, $C_{11}$–$C_{15}$ Pareth-13 and $C_{11}$–$C_{15}$ Pareth-14. PEG 40 hydrogenated castor oil is commercially available under the tradename Cremophor (RTM) from BASF. PEG 7 glyceryl cocoate and PEG 20 glyceryl laurate are commercially available from Henkel under the tradenames Cetiol (RTM) HE and Lamacit (RTM) GML 20 respectively. $C_9$–$C_{11}$ Pareth-8 is commercially available from Shell Ltd under the tradename Dobanol (RTM) 91-8. Particularly preferred for use herein are polyethylene glycol ethers of ceteryl alcohol such as Ceteareth 25 which is available from BASF under the trade name Cremaphor A25.

Also suitable for use herein are nonionic surfactants derived from composite vegetable fats extracted from the fruit of the Shea Tree (Butyrospermum Karkii Kotschy) and derivatives thereof. Similarly, ethoxylated derivatives of Mango, Cocoa and Illipe butter may be used in compositions according to the invention. Although these are classified as ethoxylated nonionic surfactants it is understood that a certain proportion may remain as non-ethoxylated vegetable oil or fat.

Other suitable oil-derived nonionic surfactants include ethoxylated derivatives of almond oil, peanut oil, rice bran oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grapeseed oil, and sunflower seed oil.

(iii) Amphoteric Surfactants

Amphoteric surfactants suitable for use in the compositions of the invention include:

(a) imidazolinium surfactants of formula (VII)

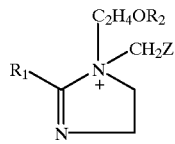

wherein $R_1$ is $C_7$–$C_{22}$ alkyl or alkenyl, $R_2$ is hydrogen or $CH_2Z$, each $Z$ is independently $CO_2M$ or $CH_2CO_2M$, and M is H, alkali metal, alkaline earth metal, ammonium or alkanolammonium; and/or ammonium derivatives of formula (VIII)

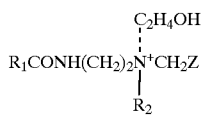

wherein $R_1$, $R_2$ and $Z$ are as defined above;

(b) aminoalkanoates of formula (IX)

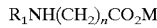

iminodialkanoates of formula (X)

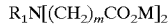

and iminopolyalkanoates of formula (XI)

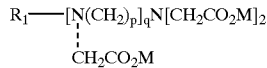

wherein n, m, p, and q are numbers from 1 to 4, and $R_1$ and M are independently selected from the groups specified above; and (c) mixtures thereof.

Suitable amphoteric surfactants of type (a) are marketed under the trade name Miranol and Empigen and are understood to comprise a complex mixture of species. Traditionally, the Miranols have been described as having the general formula (VII), although the CTFA Cosmetic Ingredient Dictionary, 3rd Edition indicates the non-cyclic structure (VIII) while the 4th Edition indicates yet another structural isomer in which $R_2$ is O-linked rather than N-linked. In practice, a complex mixture of cyclic and non-cyclic species is likely to exist and both definitions are given here for sake of completeness. Preferred for use herein, however, are the non-cyclic species.

Examples of suitable amphoteric surfactants of type (a) include compounds of formula XII and/or XIII in which $R_1$ is $C_8H_{17}$ (especially iso-capryl), $C_9H_{19}$ and $C_{11}H_{23}$ alkyl. Especially preferred are the compounds in which $R_1$ is $C_9H_{19}$, Z is $CO_2M$ and $R_2$ is H; the compounds in which $R_1$ is $C_{11}H_{23}$, Z is $CO_2M$ and $R_2$ is $CH_2CO_2M$; and the compounds in which $R_1$ is $C_{11}H_{23}$, Z is $CO_2M$ and $R_2$ is H.

In CTFA nomenclature, materials suitable for use in the present invention include cocoamphocarboxypropionate, cocoamphocarboxy propionic acid, and especially cocoamphoacetate and cocoamphodiacetate (otherwise referred to as cocoamphocarboxyglycinate). Specific commercial products include those sold under the trade names of Ampholak 7TX (sodium carboxy methyl tallow polypropyl amine), Empigen CDL60 and CDR 60 (Albright & Wilson), Miranol H2M Conc. Miranol C2M Conc. N.P., Miranol C2M Conc. O.P., Miranol C2M SF, Miranol CM Special (Rhône-Poulenc); Alkateric 2CIB (Alkaril Chemicals); Amphoterge W-2 (Lonza, Inc.); Monateric CDX-38, Monateric CSH-32 (Mona Industries); Rewoteric AM-2C (Rewo Chemical Group); and Schercotic MS-2 (Scher Chemicals). Further examples of amphoteric surfactants suitable for use herein include Octoxynol-1 (RTM), polyoxethylene (1) octylphenyl ether; Nonoxynol-4 (RTM), polyoxyethylene (4) nonylphenyl ether and Nonoxynol-9, polyoxyethylene (9) nonylphenyl ether.

It will be understood that a number of commercially-available amphoteric surfactants of this type are manufactured and sold in the form of electroneutral complexes with, for example, hydroxide counterions or with anionic sulfate or sulfonate surfactants, especially those of the sulfated $C_8$–$C_{18}$ alcohol, $C_8$–$C_{18}$ ethoxylated alcohol or $C_8$–$C_{18}$ acyl glyceride types. Note also that the concentrations and weight ratios of the amphoteric surfactants are based herein on the uncomplexed forms of the surfactants, any anionic surfactant counterions being considered as part of the overall anionic surfactant component content.

Examples of preferred amphoteric surfactants of type (b) include N-alkyl polytrimethylene poly-, carboxymethylamines sold under the trade names Ampholak X07 and Ampholak 7CX by Berol Nobel and also salts, especially the triethanolammonium salts and salts of N-lauryl-beta-amino propionic acid and N-lauryl-imino-dipropionic acid. Such materials are sold under the trade name Deriphat by Henkel and Mirataine by Rhône-Poulenc.

(iv) Zwitterionic Surfactants

Water-soluble auxiliary zwitterionic surfactants suitable for inclusion in the compositions of the present invention include alkyl betaines of the formula $R_5R_6R_7N^+$ $(CH_2)_n$ $CO_2M$ and amido betaines of the formula (XII) below:

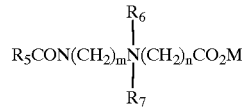

wherein $R_5$ is $C_{11}$–$C_{22}$ alkyl or alkenyl, $R_6$ and $R_7$ are independently $C_1$–$C_3$ alkyl, M is H, alkali metal, alkaline earth metal, ammonium or alkanolammonium, and n, m are each numbers from 1 to 4. Preferred betaines include cocoamidopropyldimethylcarboxymethyl betaine, laurylamidopropyldimethylcarboxymethyl betaine and Tego betaine (RTM).

Water-soluble auxiliary sultaine surfactants suitable for inclusion in the compositions of the present invention include alkyl sultaines of the formula (XIII) below:

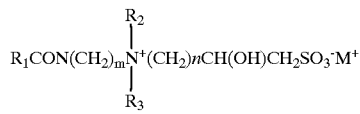

wherein $R_1$ is $C_7$ to $C_{22}$ alkyl or alkenyl, $R_2$ and $R_3$ are independently $C_1$ to $C_3$ alkyl, M is H, alkali metal, alkaline earth metal, ammonium or alkanolammonium and m and n are numbers from 1 to 4. Preferred for use herein is coco amido propylhydroxy sultaine.

Water-soluble auxiliary amine oxide surfactants suitable for inclusion in the compositions of the present invention include alkyl amine oxide $R_5R_6R_7NO$ and amido amine oxides of the formula (XIV) below:

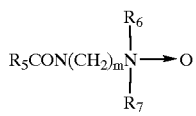

wherein $R_5$ is $C_{11}$ to $C_{22}$ alkyl or alkenyl, $R_6$ and $R_7$ are independently $C_1$ to $C_3$ alkyl, M is H, alkali metal, alkaline earth metal, ammonium or alkanolammonium and m is a number from 1 to 4. Preferred amine oxides include cocoamidopropylamine oxide, lauryl dimethyl amine oxide and myristyl dimethyl amine oxide.

The hair coloring compositions of the present invention may, in addition to the essential reactive hair coloring agents, optionally include other dye materials. Optional other dyes suitable for use in the hair coloring compositions and processes according to the present invention include both semi-permanent, temporary and other dyes.

Suitable optional dyes for use herein include oxidative dyes. Any oxidative dye suitable for use in dyeing hair can be used in the compositions herein, for example those mentioned in WO98/27945, incorporated herein by reference in its entirety.

Non-oxidative dyes as defined herein include the so-called 'direct action dyes', metallic dyes, metal chelate dyes, fibre reactive dyes and other synthetic and natural dyes. Various types of non-oxidative dyes are detailed in: 'Chemical and Physical Behaviour of Human Hair' 3rd Ed. by Clarence Robbins (pp250–259); 'The Chemistry and Manufacture of Cosmetics'. Volume IV. 2nd Ed. Maison G. De Navarre at chapter 45 by G. S. Kass (pp841–920); 'cosmetics: Science and Technology' 2nd Ed., Vol. II Balsam Sagarin, Chapter 23 by F. E. Wall (pp 279–343); 'The Science of Hair Care' edited by C. Zviak, Chapter 7 (pp 235–261) and 'Hair Dyes', J. C. Johnson, Noyes Data Corp., Park Ridge, U.S.A. (1973), (pp 3–91 and 113–139).

A number of additional optional materials can be added to the coloring compositions herein described each at a level of from about 0.001% to about 5%, preferably from about 0.01% to about 3%, more preferably from about 0.05% to about 2% by weight of composition. Such materials include proteins and polypeptides and derivatives thereof; water-soluble or solubilizable preservatives such as DMDM Hydantoin, Germall 115, methyl, ethyl, propyl and butyl esters of hydroxybenzoic acid, EDTA, Euxyl (RTM) K400, natural preservatives such as benzyl alcohol, potassium sorbate and bisabalol, benzoic acid, sodium benzoate and 2-phenoxyethanol; antioxidants such as sodium sulphite, hydroquinone, sodium bisulphite, sodium metabisulphite, sodium dithionite, erythrobic acid and other mercaptans; dye removers such as oxalic acid, sulphated castor oil, salicylic acid and sodium thiosulphate; $H_2O_2$ stabilisers such as tin compounds such as sodium stannate, stannic hydroxide and stannous octoate, acetanilide, phenacetin colloidal silica such as magnesium silicate, oxyquinoline sulphate, sodium phosphate, and tetrasodium pyrophosphate; and p-hydroxybenzoates; moisturising agents such as hyaluronic acid, chitin, and starch-grafted sodium polyacrylates such as Sanwet (RTM) IM-1000, IM-1500 and IM-2500 available from Celanese Superabsorbent Materials, Portsmith, Va., USA and described in U.S. Pat. No. 4,076,663 as well as methyl cellulose, starch, higher fatty alcohols, paraffin oils, fatty acids and the like; solvents; anti-bacterial agents such as Oxeco (phenoxy isopropanol); low temperature phase modifiers such as ammonium ion sources (e.g. $NH_4 Cl$); viscosity control agents such as magnesium sulfate and other electrolytes; quaternary amine compounds such as distearyl-, dilauryl-, di-hydrogenated beef tallow-, dimethyl ammonium chloride, dicetyldiethyl ammoniumethylsulphate, ditallowdimethyl ammonium methylsulphate, disoya dimethyl ammonium chloride and dicoco dimethyl ammonium chloride; hair conditioning agents such as silicones, higher alcohols, cationic polymers and the like; enzyme stabilisers such as water soluble sources of calcium or borate species; colouring agents; $TiO_2$ and $TiO_2$-coated mica; perfumes and perfume solubilizers; and zeolites such as Valfour BV400 and derivatives thereof and $Ca^{2+}/Mg^{2+}$ sequestrants such as polycarboxylates, amino polycarboxylates, polyphosphonates, amino polyphosphonates etc. and water softening agents such as sodium citrate.

The present invention is represented by the following non-limiting examples. In the examples, all concentrations are on a 100% active basis and all percentages are by weight unless otherwise stated and the abbreviations have the following designations.

EXAMPLES

Example 1

Synthesis of Monothioglycolatotriazine dye using Procion (RTM) dyes as starting materials The monothioglycolato triazine dye is prepared using the synthesis route as illustrated in Diagram 1.

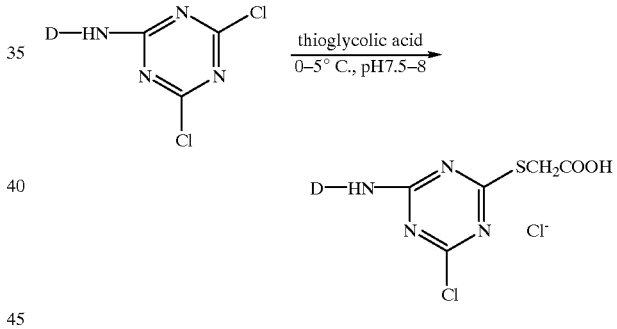

In the reaction scheme D is a chromophore and varies depending on which starting dye is used. In the present example a variety of Procion (RTM) dyes commercially available from BASF are used as starting materials, in particular, Procion Red MX-8B, Procion Yellow MX-8G and Procion Blue MX-2G.

Synthesis of monochloromonothioglycolato triazine dye

An aqueous dye solution (0.1 mol/100 ml, pH 7.5) of a purified Procion (RTM) dichlorotriazine dye is prepared. To this solution, a 0.1 mol solution of Mercaptoacetic acid is added by slow dripping at a temperature of between 0 and 5° C. After the addition of mercaptoacetic acid, the pH of the system is adjusted to 8 using sodium carbonate and HCl. The reaction is then allowed to proceed, at 0~5° C. and pH8, for 5~8 hours. For each individual dye, the required reaction time is different (7~8 hours for Procion Red MX-8B, ~6 hours for Procion Yellow MX-8G and ~5 hours for Procion Blue MX-2G). During the synthesis, a rapid pH drop is observed which can adjusted to pH 8 using buffering agents. The end-of-reaction point, for this part of the synthesis, is indicated by the pH of the reaction system remaining constant for more than 5 minutes. At this point, the dye monochloro-monothioglycolato triazine is obtained. At the end of the synthesis, the pH of the system is reduced to below pH 2. The solid monochloromonothioglycolato triazine dye compounds are then obtained following precipitation and filtration.

Example 2

Synthesis of monothioethanoltriazine dye

The monothioethanol triazine dye is prepared using the synthesis route as illustrated in Diagram 2.

Diagram 2

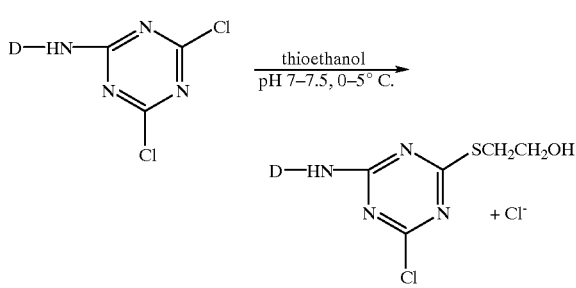

In the reaction scheme D is a chromophore and varies depending on which starting dye is used. In the present example Procion (RTM) Red MX-8G is used as the starting material, but other suitable dichlorotriazine dye compounds can also be used as starting materials such as Procion Yellow MX-8G and Procion Blue MX-2G.

0.1 mole of Procion Red MX-8G dye is dissolved in 150 ml of distilled water and added to a flask. The flask is placed in an ice-water bath. 0.1 moles of thioethanol is then added drop-wise, to the reaction mixture under stirring. The total addition time is one hour. The pH of the reaction scheme is maintained at pH 7–7.5 and the temperature of the reaction system 0–5° C. during addition of thioethanol. The reaction is then allowed to proceed at 0–5° C. and pH 7.5–8 (which is corrected using sodium carbonate and HCl) for 5 hours. The endpoint of the reaction is indicated by the pH remaining constant for more than 5 minutes. At this point, the monochloromonothioethanol triazine dye is obtained. Using 6N HCl, the pH of the system is then reduced to below pH2 to terminate the reaction. KCl (35% of the total solution) is then added to the reaction mixture in order to precipitate the dye. Filtration using Whatman filter paper follows. The precipitate is then washed with acetone for 4–5 times (50 ml of acetone used each time) to obtain the final dye product.

Example 3

Synthesis of monothiosuccinate triazine dye

The monothiosuccinate triazine dye is prepared using the synthesis route as illustrated in Diagram 3.

Diagram 3

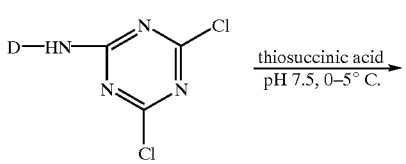

-continued

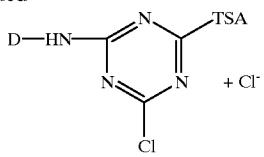

In the reaction scheme D is a chromophore and varies depending on which starting dye is used. In the present example Procion (RTM) Red MX-8G is used as the starting material, but other suitable dichlorotriazine dye compounds can also be used as starting materials, such as Procion (RTM) Yellow MX-8G and Procion (RTM) Blue MX-2G. In the above reaction scheme TSA denotes thiosuccinate attached to the ring via its sulphur atom.

0.1 moles of pure Procion Red MX-8G dye and 150 ml of distilled water are introduced into a 400 ml flask. The flask is placed in an ice-water bath. 0.1 moles of thiosuccinic acid is then added dropwise with stirring. The addition time is 1–1.5 hours. The pH of the reaction system is maintained at pH7.5 and the temperature of the reaction system is 0–5° C. throughout the addition of thiosuccinic acid.

The reaction is then allowed to proceed, at 0–5° C. and pH7.5–8 (which is corrected using sodium carbonate and HCl) for 6 hours. The endpoint of the reaction for this part of the synthesis is indicated by the pH of the reaction system remaining constant for more than 5 minutes. At this point, the dye monochloromonothiosuccinate triazine dye is obtained. Using 6N HCl, the pH of the system is then reduced to below pH 2 to terminate the reaction. KCl (35% of the total solution) is then added to the reaction mixture in order to precipitate the dye. Filtration using Whatman paper follows. The precipitate is then washed with acetone for 4–5 times (50 ml of acetone is used each time) to obtain the final dye product.

Example 4

Synthesis of mono-5-chloro-4-thioglycolato pyrimidine dye

The mono-5-chloromono4-thioglycolato pyrimidine dye is prepared using the synthesis route as illustrated in Diagram 4.

Diagram 4

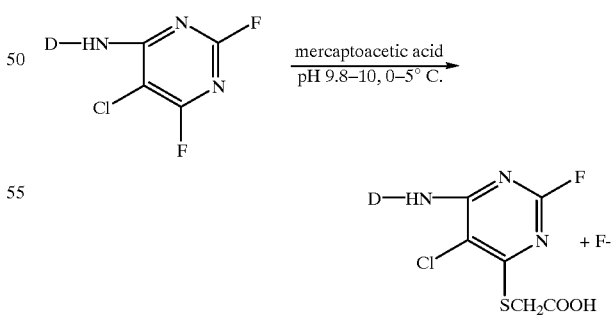

In the reaction scheme D is a chromophore and varies depending on which starting dye is used. In the present example Drimalan (RTM) Red FB dye commercially available from Clariant is used as starting material. However, Drimalan Red FB can be substituted for any suitable difluoromonochloro pyrimidine dye such as those commercially available under the tradename Drimalan and Drimarene dyes, in particular, Drimalan Red FB, Drimalan Yellow F-R, Drimalan Blue F-G, Drimalan Blue F-B, Drimalan Yellow F-3GL, Drimalan Black F-B, Drimarene Golden Yellow R-G2R, Drimarene Blue R-GL, Drimarene Brill Red R-8B, and Drimarene Brill Red K-4BL. In the above reaction scheme TGA denotes a thioglycolato moiety.

0.1 moles of Drimalan Red F-B dye and distilled water are introduced into a flask. The flask is then placed in an ice-water bath. 0.1 moles of mercaptoacetic acid is then added dropwise to the reaction mixture with stirring. The total addition time is 1–1.5 hours. The pH of the reaction mixture is maintained at pH 9.8–10 and at a temperature of 0–5° C. throughout the addition of mercaptoacetic acid.

The reaction is then allowed to proceed at 5° C. and pH 9.8–10 (which is corrected using sodium carbonate and HCl) for 15 hours. The end-of-reaction point for this part of the synthesis is indicated by the pH of the reaction system remaining constant for more than 5 minutes. At this point, the mono-5-chloro-2-fluoro-mono-4-thioglycolato pyrimidine dye is obtained. Using 6N HCl the pH of the system is then reduced to below pH2 to terminate the reaction. KCl ($\cong$35% of the total solution) is then added to the reaction mixture in order to precipitate the dye. Filtration using Whatman filter paper follows. The precipitate is then washed with acetone for 4–5 times ($\cong$50 ml of acetone used each time) to obtain the mono-5-chloro-2-fluoro-mono4-thioglycolato pyrimidine dye.

Example 5

Dye solutions can be made up using compounds prepared according to Example 1 and packaged in a suitable bottle-type package.

| Ingredients | % |
| --- | --- |
| Auburn Dye | |
| Urea | 10.00 |
| Cocamidopropyl Betaine | 0.80 |
| Dye prepared according to Example 1 using Procion Red MX-BB | 0.23 |
| Dye prepared according to Example 1 using Procion Yellow MX-GR | 0.42 |
| Dye prepared according to Example 1 using Procion Blue Mx-2G, 125 | 0.35 |
| Thioglycolic Acid 80% | 9.26 |
| Triethanolamine 99% | 50.74 |
| Ammonium Hydroxide 29% | 9.00 |
| Water | to 100 |
| Light Brown Dye | |
| Urea | 10.00 |
| Cocamidopropyl Betaine | 0.80 |
| Dye prepared according to Example 1 using Procion Red MX-SB | 0.010 |
| Dye prepared according to Example 1 using Procion Yellow MX-GR | 0.226 |
| Dye prepared according to Example 1 using Procion Blue MX-2G, 125 | 0.678 |
| Thioglycolic Acid 80% | 9.26 |
| Triethanolamine 99% | 50.74 |
| Ammonium Hydroxide 29% | 9.00 |
| Water | to 100 |

-continued

| Ingredients | % |
| --- | --- |
| Champagne Blonde | |
| Urea | 10.00 |
| Cocamidopropyl Betaine | 0.80 |
| Dye prepared according to Example 1 using Procion Red MX-8B | 0.023 |
| Dye prepared according to Example 1 using Procion Yellow MX-GR | 0.465 |
| Dye prepared according to Example 1 using Procion Blue MX-2G, 125 | 0.512 |
| Thioglycolic Acid 80% | 9.26 |
| Triethanolamine 99% | 50.74 |
| Ammonium Hydroxide 29% | 9.00 |
| Water | to 100 |
| Auburn Dye | |
| Urea | 10.00 |
| Cocamidopropyl Betaine | 0.80 |
| Dye prepared according to Example 1 using Procion Red MX-8B | 0.23 |
| Dye prepared according to Example 1 using Procion Yellow MX-GR | 0.42 |
| Dye prepared according to Example 1 using Procion Blue MX-2G, 125 | 0.35 |
| Thioglycolic Acid 99% | 7.48 |
| Ammonium Hydroxide 29% | 11.48 |
| Water | to 100 |
| Light Brown Dye | |
| Urea | 10.00 |
| Cocamidopropyl Betaine | 0.80 |
| Dye prepared according to Example 1 using Procion Red MX-8B | 0.010 |
| Dye prepared according to Example 1 using Procion Yellow MX-GR | 0.226 |
| Dye prepared according to Example 1 using Procion Blue MX-2G, 125 | 0.678 |
| Thioglycolic Acid 99% | 7.48 |
| Ammonium Hydroxide 29% | 11.48 |
| Water | to 100 |
| Champagne Blonde | |
| Urea | 10.00 |
| Cocamidopropyl Betaine | 0.80 |
| Dye prepared according to Example 1 using Procion Red MX-8B | 0.023 |
| Dye prepared according to Example 1 using Procion Yellow MX-GR | 0.465 |
| Dye prepared according to Example 1 using Procion Blue MX-2G, 125 | 0.678 |
| Thioglycolic Acid 99% | 7.48 |
| Ammonium Hydroxide 29% | 11.48 |
| Water | to 100 |
| Auburn Dye | |
| Urea | 10.00 |
| Cocamidopropyl Betaine | 0.80 |
| Dye prepared according to Example 1 using Procion Red Mx-8B | 0.23 |
| Dye prepared according to Example 1 using Procion Yellow MX-GR | 0.42 |

| Ingredients | % |
|---|---|
| *-continued* | |
| Dye prepared according to Example 1 using Procion Blue MX-26, 125 | 0.35 |
| Thioglycolic Acid 99% | 7.48 |
| Sodium Hydroxide 47% | 8.38 |
| Water | to 100 |
| *Light Brown Dye* | |
| Urea | 10.00 |
| Cocamidopropyl Betaine | 0.80 |
| Dye prepared according to Example 1 using Procion Red MX-8B | 0.010 |
| Dye prepared according to Example 1 using Procion Yellow MX-GR | 0.226 |
| Dye prepared according to Example 1 using Procion Blue MX-2G, 125 | 0.678 |
| Thioglycolic Acid 99% | 7.48 |
| Sodium Hydroxide 47% | 8.38 |
| Water | to 100 |
| *Champagne Blonde* | |
| Urea | 10.00 |
| Cocamidopropyl Betaine | 0.80 |
| Dye prepared according to Example 1 using Procion Red MX-SB | 0.023 |
| Dye prepared according to Example 1 using Procion Yellow MX-GR | 0.465 |
| Dye prepared according to Example 1 using Procion Blue MX-2G, 125 | 0.512 |
| Thioglycolic Acid 99% | 7.48 |
| Sodium Hydroxide 47% | 8.38 |
| Water | to 100 |

Any of the compounds prepared according to Examples 1 to 4 can be substituted for the compounds in the dye compositions above.

In particular, the packaged hair colouring compositions of the examples provide improvements in terms of consumer acceptance since no admixing of ingredients is necessary before dyeing, and improved wash fastness.

What is claimed is:

1. Packaged hair colouring composition comprising a stable aqueous hair colouring composition comprising a compound of formula (I):

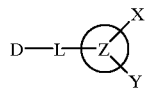

wherein D is a chromophore;

X and Y are independently selected from the group consisting of halogen and —SR', provided that at least one of X and Y is —SR', wherein R' is selected from the group consisting of H, $C_1$–$C_4$ alkyl, $(CH_2)_n COOH$, $(CH_2)_n CONH_2$, $(CH_2)_n SO_3 H$, $(CH_2)_n COOM$, $(CH_2)_n PO_3 H$, $(CH_2)_n OH$, $(CH_2)_n SSO_3^-$, $(CH_2)_n NR''_2$, $(CH_2)_n N^+R''_3$, $PhSSO_3^-$, $PhSO_3 H$, $PhPO_3 H$, $PhNR''_2$, $PhN^+R''_3$, —CN, $SO_3^-$, $(CH_2)_2 CH(SH)R''(CH_2)_3 COOH$, —$CH_2 CHOHCH_2 SH$, and

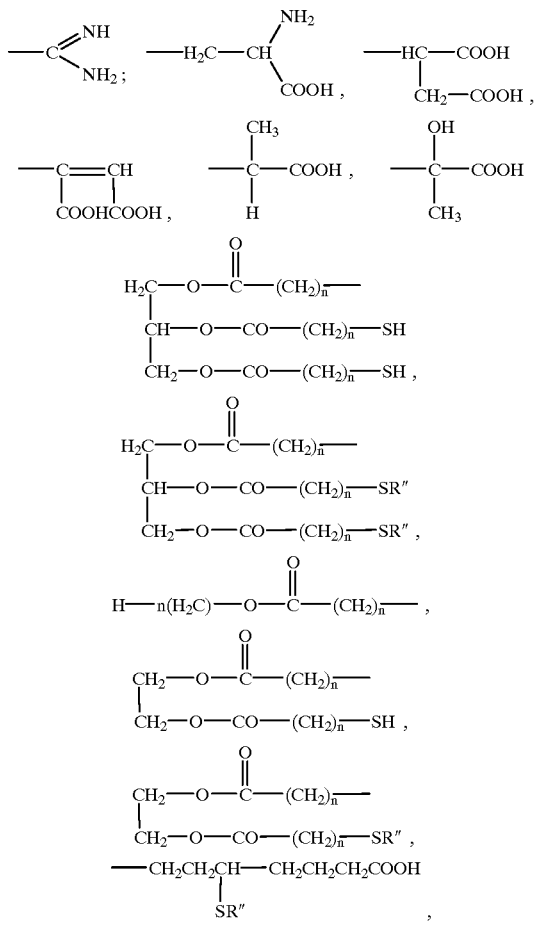

—$CH_2 CH_2 NH_2$;

n is an integer in the range of 1 to 4 wherein within the same molecule n is not necessarily the same integer; and M is a cation of alkaline earth metal, alkali metal, $NH_4^+$ or $NR''_3^+$;

L is a linking moiety;

Z is pyrimidine or triazine;

R" is C1–C4 alkyl;

and a package for said hair colouring composition.

2. Packaged hair colouring composition according to claim 1 wherein Z is triazine.

3. Packaged hair colouring composition according to claim 1 wherein both X and Y are —SR'.

4. Packaged hair colouring composition according to claim 1 wherein R' is CH2COOH.

5. Packaged hair colouring composition according to claim 1 wherein L is selected from NR, NRC=O, C(O)NR, NRSO2 and —SO2NR wherein R is H or $C_1$–$C_4$ alkyl which can be substituted by halogen, hydroxyl, cyano, $C_1$–$C_4$ alkoxy, $C_2$–$C_5$ alkoxycarbonyl, carboxyl, sulfamoyl, sulfo or sulfato.

6. Packaged hair colouring composition according to claim 5 wherein R is $C_1$–$C_4$ alkyl which can be substituted by fluorine or chlorine.

7. Packaged hair colouring composition according to claim 5 wherein L is NR.

8. Packaged hair colouring composition according to claim 7 wherein R is C1–C4 alkyl or H.

9. Packaged hair colouring composition according to claim 8 wherein R is H.

10. A hair colouring composition comprising:

(a) a purified reactive dye compound in particulate form having the formula (I):

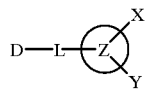

wherein D is a chromophore;

X and Y are independently selected from the group consisting of halogen and —SR', provided that at least one of X and Y is —SR', wherein R' is selected from the group consisting of H, $C_1$–$C_4$ alkyl, $(CH_2)_n COOH$, $(CH_2)_n CONH_2$, $(CH_2)_n SO_3H$, $(CH_2)_n COOM$, $(CH_2)_n PO_3H$, $(CH_2)_n OH$, $(CH_2)_n SSO_3^-$, $(CH_2)_n NR''_2$, $(CH_2)_n N^+R''_3$, $PhSSO_3^-$, $PhSO_3H$, $PhPO_3H$, $PhNR''_2$, $PhN^+R''_3$, —CN, $SO_3^-$, $(CH_2)_2CH(SH)R''(CH_2)_3COOH$, —$CH_2CHOHCH_2SH$, and

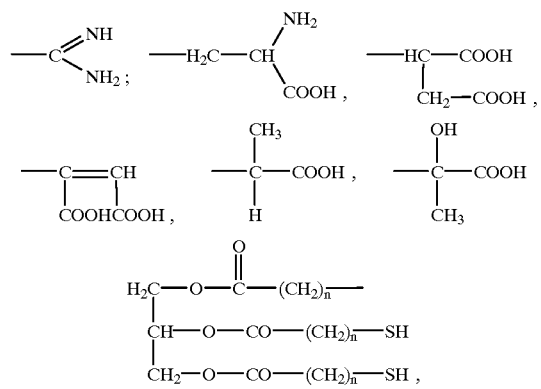

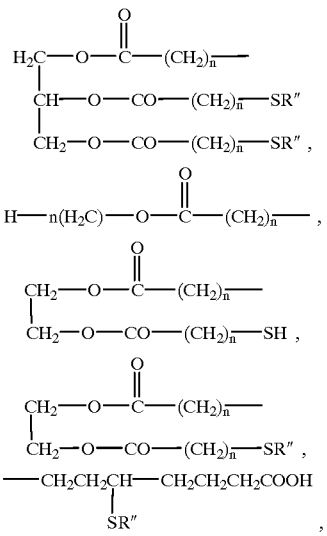

—$CH_2CH_2NH_2$;

n is an integer in the range of 1 to 4 wherein within the same molecule n is not necessarily the same integer; and M is a cation of alkaline earth metal, alkali metal, $NH_4^+$ or $NR''_3^+$;

L is a linking moiety;

Z is pyrimidine or triazine;

R" is C1–C4 alkyl; and (b) a solvent.

11. A hair colouring composition according to claim 10 wherein the solvent comprises water.

* * * * *